United States Patent
Villain et al.

(10) Patent No.: US 11,992,825 B2
(45) Date of Patent: May 28, 2024

(54) ADSORPTION MEDIUM, METHOD FOR PRODUCTION THEREOF, AND USE THEREOF FOR PURIFICATION OF BIOMOLECULES

(71) Applicant: Sartorius Stedim Biotech GmbH, Göttingen (DE)

(72) Inventors: Louis Villain, Hannover (DE); Florian Taft, Hannover (DE); Jan Schwellenbach, Göttingen (DE)

(73) Assignee: Sartorius Stedim Biotech GmbH, Göttingen (DE)

( * ) Notice: Subject to any disclaimer, the term of this patent is extended or adjusted under 35 U.S.C. 154(b) by 218 days.

(21) Appl. No.: 15/758,012

(22) PCT Filed: Jul. 7, 2016

(86) PCT No.: PCT/EP2016/001168
§ 371 (c)(1),
(2) Date: Mar. 7, 2018

(87) PCT Pub. No.: WO2017/041868
PCT Pub. Date: Mar. 16, 2017

(65) Prior Publication Data
US 2018/0243724 A1  Aug. 30, 2018

(30) Foreign Application Priority Data
Sep. 10, 2015 (DE) .................. DE10 2015 011 884

(51) Int. Cl.
*B01J 20/289* (2006.01)
*B01D 15/20* (2006.01)
(Continued)

(52) U.S. Cl.
CPC ............ *B01J 20/289* (2013.01); *B01D 15/20* (2013.01); *B01J 20/321* (2013.01);
(Continued)

(58) Field of Classification Search
None
See application file for complete search history.

(56) References Cited

U.S. PATENT DOCUMENTS

| 4,388,448 A | 6/1983 | Melby |
| 7,955,795 B2 * | 6/2011 | Kumar ................. C12Q 1/6844 435/6.12 |

(Continued)

FOREIGN PATENT DOCUMENTS

| EP | 0 295 073 | 12/1988 |
| EP | 1 224 975 | 7/2002 |

(Continued)

OTHER PUBLICATIONS

Noel, S., et al., "Quantification of Primary Amine Groups Available for Subsequent Biofunctionalization of Polymer Surfaces", Bioconjugate Chemistry, 2011, vol. 22, pp. 1690-1699.
(Continued)

*Primary Examiner* — Kara M Peo
(74) *Attorney, Agent, or Firm* — McDonnell Boehnen Hulbert & Berghoff LLP

(57) ABSTRACT

The present invention relates to an adsorption medium including polymeric space elements which have been bonded to the surface of the chromatography matrix, and polymer chains containing chromatographically active centers, wherein the polymer chains have been bonded to the polymeric spacer elements, as well as to a method for the production thereof, and to the use of the adsorption medium for the purification of biomolecules.

21 Claims, 6 Drawing Sheets

(51) Int. Cl.
  *B01J 20/32* (2006.01)
  *C07K 1/16* (2006.01)
  *C07K 1/18* (2006.01)
  *C12N 9/36* (2006.01)
  *B01D 15/36* (2006.01)

(52) U.S. Cl.
  CPC ....... *B01J 20/3219* (2013.01); *B01J 20/3278* (2013.01); *B01J 20/328* (2013.01); *B01J 20/3293* (2013.01); *C07K 1/16* (2013.01); *C07K 1/18* (2013.01); *C12N 9/2462* (2013.01); *B01D 15/362* (2013.01)

(56) References Cited

U.S. PATENT DOCUMENTS

| | | | |
|---|---|---|---|
| 10,407,713 B2* | 9/2019 | Porschewski | C12Q 1/6806 |
| 2014/0263011 A1* | 9/2014 | Thiyagarajan | B01J 20/327 210/198.2 |
| 2014/0274790 A1* | 9/2014 | Ito | C07K 1/22 506/9 |
| 2014/0316108 A1 | 10/2014 | Wirth et al. | |
| 2015/0218208 A1 | 8/2015 | Koguma et al. | |
| 2016/0083419 A1 | 3/2016 | Taniguchi et al. | |

FOREIGN PATENT DOCUMENTS

| | | |
|---|---|---|
| EP | 1224975 A1 | 7/2002 |
| EP | 2 153 877 A1 | 7/2008 |
| WO | 2014/034644 A1 | 3/2014 |
| WO | 2014067605 A1 | 5/2014 |
| WO | WO 2014/067605 | 5/2014 |
| WO | 2014/171437 A1 | 10/2014 |

OTHER PUBLICATIONS

Qian, X., et al., "Preparation of High-Capacity, Weak Anion-Exchange Membranes by Surface-Initiated Atom Transfer Radical Polymerization of Poly(glycidyl methacrylate) and Subsequent Derivatization with Diethylamine", Applied Surface Science, Apr. 15, 2013, vol. 271, pp. 240-247.
Hermanson, G.T., et al., "Immobilized Affinity Ligand Techniques", Academic Press Inc., 1992, pp. vii-xv and 178-181.
P. Kosiol, Master's Thesis, Georg-August Universitat Gottingen, 2013.
Xiao, Jihua, "Investigation of Fiber Splitting in Side-by-Side Bicomponent Meltblown Nonwoven Webs by Additive Applications", TRACE: Tennessee Research and Creative Exchange, Master's Thesis, University of Tennessee, Dec. 2004, pp. 1-106.
Sigma-Aldrich, "Poly(glycidyl methacrylate)", pp. 1-2. [Retrieved from the internet on Apr. 9, 2021].
Benaglia, M., et al., "Poly(glycidyl methacrylate): A Highly Versatile Polymeric Building Block for Postpolymerization Modifications", Polym. Chem., 2013, vol. 4, pp. 124-132.
Funktionelle Gruppen, Online https://roempp.thieme.de/lexicon/RD-06-02112?searchterm=funktionelle+gruppen&context=search, downloaded on Jun. 22, 2022.
Office Action issued in German Patent Application No. 10 2015 011 884.6 dated Jun. 23, 2022.

* cited by examiner

ADSORPTION MEDIUM, METHOD FOR PRODUCTION THEREOF, AND USE THEREOF FOR PURIFICATION OF BIOMOLECULES

This application is a section 371 national filing of International Patent Application No. PCT/EP2016/001168, filed Jul. 7, 2016 which claims priority from German patent application no. 10 2015 011 884.6, filed Sep. 10, 2015.

FIELD OF THE INVENTION

The present invention relates to an adsorption medium, especially a chromatography medium, to a method for the production thereof, and to the use of the adsorption medium according to the invention or of an adsorption medium produced according to the invention for the purification of biomolecules.

BACKGROUND OF THE INVENTION

"Adsorption medium" refers to adsorbents which have functional surface groups, often also referred to as "chromatographically active centers" and/or "ligands", which can selectively form bonds with certain components of fluids. Target substance(s) and/or contaminant(s) are, according to the invention, referred to as "substances to be adsorbed", it also being possible for multiple different substances to be involved. Substances to be adsorbed can be individual molecules, complexes or particles which are preferably proteins or other substances of biological origin.

By way of example, ligands which interact with the substance(s) to be adsorbed include ion exchangers, chelating agents and heavy metal chelates, thiophilic, hydrophobic ligands of various chain lengths and configurations, reversed-phase systems, dye ligands, affinity ligands, amino acids, coenzymes, cofactors and the analogs thereof, substrates and the analogs thereof, endocrine and exocrine substances, such as hormones and substances which act like hormones, effectors and the analogs thereof, enzyme substrates, enzyme inhibitors and the analogs thereof, fatty acids, fatty acid derivatives, conjugated fatty acids and the analogs thereof, nucleic acids, such as DNA, RNA and the analogs and derivatives thereof (single-stranded, double-stranded and/or multistranded), and also peptide nucleic acids and the derivatives thereof, viruses, virus particles, monomers and the analogs and derivatives thereof, oligomers to polymers and the analogs and derivatives thereof, high-molecular-weight carbohydrates, which can be linear or branched, nonsubstituted or substituted, polymeric glycoconjugates, such as heparin, amylose, cellulose, chitin, chitosan and the monomers and oligomers thereof and derivatives and analogs thereof, lignin and the derivatives and analogs thereof, other biological/chemical ligands, such as oligopeptides and polypeptides, for example proteins and their oligomers, multimers, subunits and also parts thereof, especially lectins, antibodies, fusion proteins, haptens, enzymes and subunits and also parts thereof, structural proteins, receptors and effectors and also parts thereof, additionally xenobiotics, pharmaceuticals and active pharmaceutical ingredients, alkaloids, antibiotics, biomimetics, etc.

An adsorbent can also simultaneously bear two or more types of the functional groups on its inner and outer surface.

The binding to the adsorbent of the substances to be adsorbed can be reversible or irreversible; in any case, it allows their removal from the fluids, which are aqueous liquids for example and which are hereinafter called "media". The desorption and the associated rinsing steps, etc., are subsumed under the term "elution", and the medium used for the elution is the "eluent". The components can be one or more target substances and/or one or more contaminants. "Target substances" are substances of value which are to be recovered from the medium in enriched or pure form. Target products can, for example, be recombinant proteins, such as, for example, monoclonal antibodies. "Contaminants" are substances, the absence or removal of which from the fluid is necessary or desirable for technical, regulatory or other reasons. Contaminants can, for example, be viruses, proteins, amino acids, nucleic acids, endotoxins, protein aggregates, ligands or the parts thereof. For the removal of contaminants, which is referred to as "negative adsorption", the adsorption can (must) proceed irreversibly if the adsorbent is to be used just once. In the case of the adsorption of the target substance(s), the process must proceed reversibly. It is possible to carry out either a mere enrichment or a separation into multiple target substances, and for the latter it is possible for the adsorption, the desorption or both to be carried out selectively.

The process is referred to as adsorptive substance separation or chromatography. Conventional chromatography adsorbents are either in particulate form and used in the form of packed beds in columns, or are in the form of adsorption membranes, which are usually located in modules, the designs of which are in line with the designs that are customary in membrane filtration (e.g., spiral-wound module, stacked module, etc.). The basic requirement of lowest possible nonspecific adsorption is usually common to all adsorbents.

As stated above, a multiplicity of synthetic and natural ligands is known in the prior art. The bonding of the ligand to the support can be preceded by an "activation" of the support, i.e., the introduction of reactive, functional groups capable of spontaneously bonding the ligand. In relatively rare cases, the ligand itself has a reactive group, such as, for example, the reactive dyes from the textile industry that serve as dye ligands. Methods for bonding functional groups are known per se to a person skilled in the art (e.g., from Greg T. Hermanson, A. Krishna Mallia, Paul K. Smith, Immobilized Affinity Ligand Techniques, Academic Press, INC, 1992).

The filtration, purification or removal of biomolecules such as proteins, amino acids, nucleic acids, viruses or endotoxins from liquid media is of great interest to the biopharmaceutical industry. The majority of contaminant-removal applications are currently run using conventional chromatography gels or chromatography membranes.

For example, WO 2014/171437 A1 and WO 2014/034644 A1 describe porous chromatography media for ion-exchange chromatography, for example for the purification of antibodies, wherein the media can be membranes, fibers or beads. In this connection, both WO 2014/171437 A1 and WO 2014/034644 A1 teach the application of graft chains composed of copolymers to porous surfaces of chromatography matrices by atom transfer radical polymerization (ATRP), wherein the graft chains are directly fixed on the porous surface. In this connection, the graft chains composed of copolymers bear the chromatographically active centers (ligands), which can then form a selective bond with the substances to be adsorbed.

However, the adsorption media known in the prior art frequently exhibit, in the case of large target molecules, a low accessibility to the polymer chains bearing the chromatographically active centers. Therefore, in the event of a binding competition between small and large target molecules, smaller target molecules are, undesirably, preferentially bound. Moreover, the chromatographically active centers (ligands) are frequently not optimally utilized as binding sites, meaning that there is a high demand for ligands in the polymer layer, and this can lead to high production costs.

SUMMARY OF THE INVENTION

It is therefore an object of the invention to provide an adsorption medium which has, in the case of large target molecules, an increased accessibility to the polymer chains bearing the chromatographically active centers, which binds large and small target molecules to the same extent, and in which the chromatographically active centers (ligands) can be optimally utilized as binding sites, meaning that the number of ligands in the adsorption medium can be reduced.

This object is achieved by the embodiments of the present invention that are characterized in the claims.

DETAILED DESCRIPTION OF THE INVENTION

Figure 1:
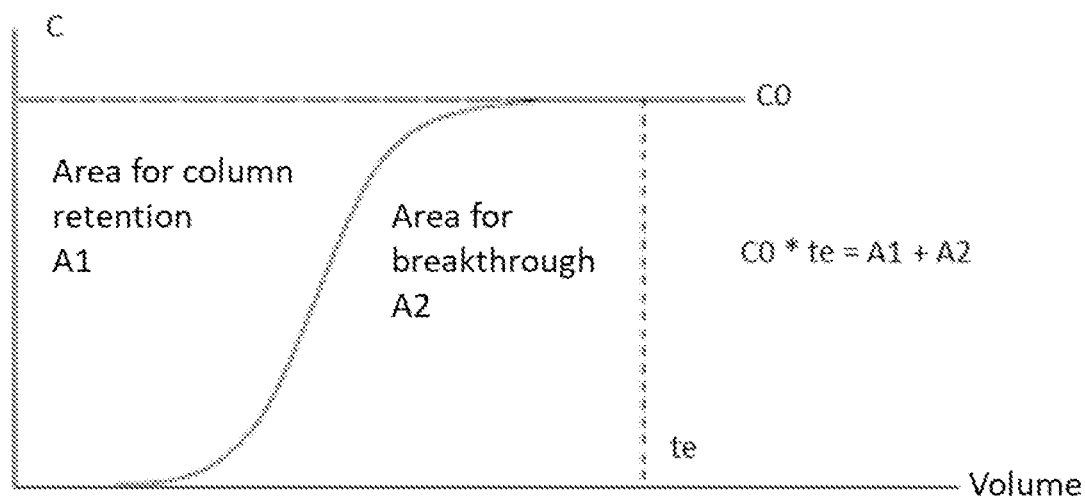
FIG. 1: Schematic breakthrough of a titration with 10 mM HCl solution.

More particularly, the invention provides an adsorption medium, especially a chromatography medium, comprising
 a chromatography matrix;
 polymeric spacer elements which have been bonded to the surface of the chromatography matrix; and
 polymer chains containing chromatographically active centers, wherein the polymer chains have been bonded to the polymeric spacer elements.

In the context of the present invention, the term "chromatography matrix" is understood to mean any material which can be used for chromatographic methods as support material of the stationary phase. The chromatography matrix of the present invention is not subject to any particular restriction, so long as it has, on its surface, functional groups to which the polymeric spacer elements can be bonded or can have been bonded. Therefore, according to the invention, it is possible to use either a chromatography matrix which originally has functional groups (e.g., polyester fibers), or a chromatography matrix in which functional groups were introduced by a surface modification known to a person skilled in the art. In this connection, known surface modifications are, for example, an activation by means of plasma treatment, electron beam treatment, gamma radiation treatment, hydrolysis, aminolysis, oxidation, reduction, reaction with functional carbenes and/or nitrenes, etc.

According to one embodiment of the present invention, the chromatography matrix has from 1.5 to 30 functional groups per $nm^2$ of specific surface area of the chromatography matrix, i.e., the (functional) group density is preferably from 1.5 to 30 $nm^{-2}$ or from 1.5 to 30 $1/nm^2$. According to the invention, the term "specific surface area" encompasses the entirety of all surfaces present in the chromatography matrix, i.e., including those situated within existing pores. The (functional) group density based on the specific surface area can be calculated from the specific surface area of the chromatography medium and the (functional) group density based on the mass of the chromatography medium. If the functional groups of the chromatography matrix are amine groups, the group density is, according to the invention, referred to as "amine group density".

According to one embodiment of the present invention, the chromatography matrix comprises a material selected from the group consisting of natural or synthetic fibers, (polymer) membranes, porous, polymeric monolithic shaped bodies, polymer gels, films, nonwovens, wovens and inorganic materials.

Examples of natural or synthetic fibers which can be used as material for the chromatography matrix of the adsorption medium according to the invention include polyester fibers (e.g., "Winged Fibers" from Allasso Industries composed of polybutylene terephthalate (PBT) or "4DG™ Fibers" from Fiber Innovation Technology composed of polyethylene terephthalate (PET)), and also fibers comprising cellulose, cellulose derivatives, nylon, polyethylene (PE), polyamide (PA), polyethersulfone (PES), polyvinylidene difluoride (PVDF), polytetrafluoroethylene (PTFE), polypropylene (PP) and polysulfone as structure-giving constituent, it being possible for these materials to be used individually or in an appropriate combination. Examples of (polymer) membranes which can be used as material for the chromatography matrix of the adsorption medium according to the invention include membranes comprising cellulose, cellulose derivatives, nylon, polyester, polyethylene (PE), polyamide (PA), polyethersulfone (PES), polyvinylidene difluoride (PVDF), polytetrafluoroethylene (PTFE), polypropylene (PP) and polysulfone as structure-giving constituent, it being possible for these materials to be used individually or in an appropriate combination. Examples of polymer gels which can be used as material for the chromatography matrix of the adsorption medium according to the invention include agarose, dextran, cellulose, polymethacrylates, polyvinyl ethers, polyacrylamides, polystyrene-divinylbenzene copolymers, silica-dextran, agarose-acrylamides and dextran-acrylamides. Examples of films and wovens include films and wovens composed of the above-mentioned polymer materials which can be used for the (polymer) membranes. Examples of nonwovens which can be used as material for the chromatography matrix of the adsorption medium according to the invention include polyester/polyamide nonwovens (e.g., "Pluratexx2317 S" from Freudenberg), and also the above polymer materials which can be used for the (polymer) membranes. Examples of inorganic materials which can be used as material for the chromatography matrix of the adsorption medium according to the invention include silicon, glasses, metal substrates such as titanium, aluminum oxide, gold and silver, and also alloys.

In the adsorption medium according to the invention, polymeric spacer elements have been bonded to the surface of the chromatography matrix, wherein the bonding between the surface of the chromatography matrix and the spacer elements is effected or has been effected preferably via the (originally present or surface-modification-generated) functional groups of the chromatography matrix. Owing to the polymeric spacer elements serving in the adsorption medium according to the invention as connection units between the chromatography matrix and the polymer chains containing chromatographically active centers (ligands), the adsorption medium according to the invention has a relatively high level of flexibility in the polymer chains containing ligands, and this advantageously significantly increases the accessibility of said polymer chains for large target molecules, since a relatively large binding volume is provided. Therefore, in the event of a binding competition between small and large target molecules, the smaller molecules are advantageously not preferred. Moreover, the chromatographically active centers (ligands) are optimally utilized, and this advantageously results in a larger value for the ratio between static protein-binding capacity and ionic capacity than in the case of adsorption media known to date. The above ratio is an inherent indicator of the saving of ligands in the production of the adsorption medium, since a high ratio value means that, even with a low ligand density, a high protein-binding capacity is already achieved, and this, with respect to the saving of especially expensive ligands, advantageously lowers the production costs for the adsorption medium according to the invention.

In the context of the present invention, the term "polymeric spacer elements" is understood to mean all polymers which can join the surface of the chromatography matrix to the polymer chains containing chromatographically active centers. The polymeric spacer elements of the present invention are not subject to any particular restriction, so long as they can be bonded (preferably) chemically, but also physically, to the surface of the chromatography matrix. According to a preferred embodiment, the polymeric spacer elements have nucleophilic functional groups, since they allow the attachment of an ATRP initiator in the preferred production method according to the invention.

According to a preferred embodiment, the polymeric spacer elements are selected from the group consisting of polyamines, polyalcohols, polythiols, poly(meth)acrylates, poly(meth)acrylamides, poly-N-alkyl(meth)acrylamides and also copolymers consisting of two or more of the above polymers, and copolymers consisting of one or more of the above polymers and of polymers which do not bear nucleophilic functional groups.

Polyamines in the context of the present invention are, for example, polyallylamine, polyvinylamine, polyethylenimine (branched or linear), poly(4-aminostyrene), chitosan, poly-L-lysine, poly(N-methylvinylamine), poly(N-methylallylamine), poly(N,N-dimethylvinylamine), poly(N,N-dimethylallylamine) and poly(oleylamines).

Polyalcohols in the context of the present invention are, for example, polyallyl alcohol, polyvinyl alcohol, polysaccharides (homoglycans and heteroglycans), poly(4-hydroxystyrene) and poly(EVOH) (EVOH=ethylene-vinyl alcohol copolymer).

Polythiols in the context of the present invention are, for example, polyvinyl thiol and polyallyl thiol.

According to the invention, the term "poly(meth)acrylate" is used as short form for "polyacrylate or polymethacrylate". Poly(meth)acrylates in the context of the present invention are, for example, poly(1-glycerol (meth)acrylate), poly(2-glycerol (meth)acrylate), poly(hydroxyethyl (meth)acrylate), poly(hydroxypropyl (meth)acrylate), poly(2-aminoethyl (meth)acrylate), poly(2-aminopropyl (meth)acrylate), poly(2-(diethylamino)ethyl (meth)acrylate), poly(ethylene glycol) (meth)acrylate, poly(hydroxybutyl (meth)acrylate), poly(glycosyloxyethyl (meth)acrylate), poly(3-(acryloyloxy)-2-hydroxypropyl (meth)acrylate), poly(3-chloro-2-hydroxypropyl (meth)acrylate), poly([tris(hydroxymethyl)methyl] (meth)acrylate), poly(2-(4-benzoyl-3-hydroxyphenoxy)ethyl (meth)acrylates).

According to the invention, all of the abovementioned poly(meth)acrylates can also be used in their analogous form as poly(meth)acrylamides and poly-N-alkyl(meth)acrylamides.

In the context of the present invention, polymers which do not bear nucleophilic functional groups are, for example, polyolefins such as polyethylene, polyfluoroethylene, polypropylene, or polymethyl methacrylate.

According to a particularly preferred embodiment, the polymeric spacer elements are polyamines, especially polyallylamine, polyvinylamine and/or polyethylenimine.

According to a further embodiment, the polymeric spacer elements do not have epoxy groups, since they can limit the flexibility of the spacer elements and thus also the flexibility of the polymer chains containing chromatographically active ligands as a result of possible intermolecular crosslinking reactions.

According to one embodiment of the present invention, the polymeric spacer elements have a molecular weight per element of from 5000 to 2 000 000 g/mol, preferably from 5000 to 50 000 g/mol.

In the adsorption medium according to the invention, the polymeric spacer elements have been bonded to both the surface of the chromatography matrix and the polymer chains containing chromatographically active centers (ligands).

In the context of the present invention, the term "polymer chains containing chromatographically active centers" is understood to mean all polymer chains which have chromatographically active centers (ligands). The polymer chains by themselves, i.e., the polymer chains without chromatographically active centers, are not subject to any particular restriction, i.e., all polymer classes such as, for example, polyolefins, polyesters, poly(meth)acrylates, etc., can be used according to the invention. Particular preference is given in this connection to poly(meth)acrylates such as, for example, glycidyl (meth)acrylate, since the adsorption medium according to the invention is, in this case, easily accessible by synthesis owing to the polymerizability of the poly(meth)acrylates via ATRP.

According to the present invention, "chromatographically active centers" or "ligands" are sites or groups in or on the polymer chains that are capable of interacting with substances to be adsorbed that are present in fluids. The chromatographically active centers in the adsorption medium according to the invention are not subject to any particular restriction. According to one embodiment of the present invention, the chromatographically active centers of the polymer chains are selected from the group consisting of anionic and cationic groups, hydrophobic groups, affinity ligands, metal chelates and reactive epoxide, aldehyde, azlactone, N-hydroxysuccinimide and/or carbodiimide groups.

According to the invention, the term "degree of grafting" is described by the following Equation (1):

$$\text{Degree of grafting [\%]} = \frac{\text{(Weight of the adsorption medium with polymer chains} - \text{Weight of the adsorption medium without polymer chains)}}{\text{(Weight of the adsorption medium without polymer chains)}} * 100\%$$

(Equation 1)

According to a preferred embodiment, the adsorption medium according to the invention has a degree of grafting of from 1% to 50%, particularly preferably from 5 to 20%. In the case of a degree of grafting of over 50%, the permeability of the adsorption medium according to the invention can disadvantageously drop.

Furthermore, the present invention provides a method for producing the adsorption medium according to the invention. The above statements concerning the adsorption medium according to the invention therefore also apply to the production method according to the invention.

The method according to the invention for producing an adsorption medium comprises the steps:
(a) providing a chromatography matrix;
(b) immobilizing polymeric spacer elements on the surface of the chromatography matrix; and
(c) immobilizing polymer chains containing chromatographically active centers on the polymeric spacer elements.

In step (a) of the method according to the invention, there is provided a chromatography matrix as described above which originally has functional groups (e.g., polyester fibers) or in which functional groups were introduced by surface modification.

In step (b) of the method according to the invention, polymeric spacer elements are immobilized on the surface of the chromatography matrix, i.e., the spacer elements are (preferably) chemically or else possibly physically bonded to the surface of the chromatography matrix via the functional groups thereof. According to the invention, the immobilization step is not subject to any particular restriction and all immobilization methods known to a person skilled in the art can be used, such as, for example, aminolyses, amide-coupling reactions, esterifications, reductive aminations and insertion reactions.

In step (c) of the method according to the invention, polymer chains containing chromatographically active centers are immobilized on the polymeric spacer elements, i.e., the polymer chains containing chromatographically active centers are chemically bonded to the polymeric spacer elements. According to the invention, the immobilization step is not subject to any particular restriction and all immobilization methods known to a person skilled in the art can be used. Step (c) of the method according to the invention is, in this case, to be understood to mean that either polymer chains already having chromatographically active centers are immobilized on the polymeric spacer elements, or polymer chains without chromatographically active centers are first immobilized on the polymeric spacer elements and chromatographically active centers are then subsequently introduced into said polymer chains. Methods for introducing chromatographically active centers into polymer chains are known to a person skilled in the art from the prior art (see, for example, X. Qian et al., Applied Surface Science 271 (2013) 240-247 and G. T. Hermanson et al., Immobilized Affinity Ligand Techniques, Academic Press, INC, 1992).

According to a preferred embodiment of the present invention, step (c) comprises the steps:
(c1) immobilizing a polymerization initiator on the polymeric spacer elements;
(c2) carrying out a spacer element-initiated polymerization of a monomer to form immobilized polymer chains on the polymeric spacer elements; and
(c3) optionally modifying the immobilized polymer chains to form chromatographically active centers on the polymer chains.

In step (c1) of the method, a polymerization initiator is immobilized on the polymeric spacer elements, i.e., a polymerization initiator is chemically bonded to the polymeric spacer elements. This is preferably realized via nucleophilic functional groups of the spacer elements, and such reactions are known to a person skilled in the art from the prior art. The polymerization initiator is not subject to any particular restriction. For example, the polymerization initiator used can be α-bromoisobutyryl bromide, 2-bromo-propionic acid, bromoacetic acid, methyl α-bromoisobutyrate, 2-bromo-2-methylpropionic acid, chloroacetic acid, 2-azidoethyl 2-bromoisobutyrate, 3-butynyl 2-bromoisobutyrate, propargyl 2-bromoisobutyrate or 2-bromoisobutyric anhydride. According to a preferred embodiment, the polymerization initiator is α-bromoisobutyryl bromide.

The initiator density, i.e., the number of immobilized polymerization initiator molecules per $nm^2$ of specific surface area of the chromatography matrix, is preferably, after step (c1) of the method according to the invention, from 1.5 to 30 $nm^{-2}$ or from 1.5 to 30 $1/nm^2$.

In step (c2) of the method, a spacer element-initiated polymerization of a monomer is carried out, the result being that immobilized polymer chains are formed on the polymeric spacer elements. According to a particularly preferred embodiment, the spacer element-initiated polymerization in step (c2) is carried out using a polymerization solution by means of an atom transfer radical polymerization (ATRP), which is known to a person skilled in the art. In this way, it can be ensured that the polymer chains have a very low degree of crosslinking and/or branching, since unwanted secondary reactions such as "back-biting" (intramolecular cyclizations of growing polymer chains), transfer reactions, etc., can be suppressed. Advantageously, very low degrees of crosslinking and/or branching of the polymer chains ensure a high level of flexibility of the polymer chains and thus also an excellent accessibility of the chromatographically active centers.

According to a particularly preferred embodiment of the method according to the invention, use is made in step (c2) of a polymerization solution comprising a proportion of not more than 3 mol % of bifunctional monomers, based on the total amount of monomers in the solution. According to the invention, the term "bifunctional monomers" is understood to mean in particular monomers having, as crosslinkable groups, epoxides, halides, isocyanates or multiple polymerizable functionalities. Advantageously, a proportion of not more than 3 mol % of bifunctional monomers in the polymerization solution, based on the total amount of monomers in the solution, leads to a particularly high level of flexibility of the polymer chains containing chromatographically active ligands, since only a low level of crosslinking of the polymer chains is generated. Therefore, the polymerization solution in step (c2) comprises preferably not more than 1.5 mol % of bifunctional monomers, based on the total amount of monomers in the solution, particularly preferably not more than 0.75 mol % and most preferably 0 mol %, i.e., there are no bifunctional monomers in the polymerization solution.

In optional step (c3) of the method, the immobilized polymer chains are modified in order to thus form chromatographically active centers on or at the polymer chains. Methods for introducing chromatographically active centers into polymer chains are known to a person skilled in the art from the prior art. For example, epoxy groups present in the polymer chains can be sulfonated with sodium sulfite and thus reacted to form a cation exchanger, or reacted with trimethylamine to form quaternary ammonium groups and thus to form an anion exchanger. If the polymer chains immobilized in step (c2) on the polymeric spacer elements already have chromatographically active centers, optional step (c3) can be dispensed with.

Furthermore, the present invention provides for the use of the adsorption medium according to the invention or of an adsorption medium produced according to the method according to the invention for the purification of biomolecules. The biomolecules to be cleaned up can, for example, be proteins, peptides, amino acids, nucleic acids, virus-like particles, viruses and/or endotoxins.

Advantageously, owing to the polymeric spacer elements, the adsorption medium according to the invention has a relatively high level of flexibility in the polymer chains containing ligands, and this significantly increases the accessibility of said polymer chains for large target molecules, since a relatively large binding volume is provided. Therefore, in the event of a binding competition between small and large target molecules, the smaller molecules are advantageously not preferred. Moreover, the chromatographically active centers (ligands) are optimally utilized, and this advantageously results in a larger value for the ratio between static protein-binding capacity and ionic capacity than in the case of adsorption media known to date. Therefore, the number of ligands or of polymer chains containing ligands can be reduced in the adsorption medium according to the invention, and this, firstly, results in a more cost-effective production and, secondly, does not disadvantageously reduce the permeability of the adsorption material. Advantageously, the method according to the invention provides said adsorption medium in a reliable manner, i.e., the high level of flexibility of the polymer chains containing ligands can be suitably realized via the method according to the invention, especially by means of an ATRP reaction. The adsorption material according to the invention is therefore outstandingly suitable for the purification of biomolecules, there being great industrial interest therein.

The present invention will be more particularly elucidated on the basis of the following nonrestrictive examples.

EXAMPLES

Methods:

Determination of amine group density via photometric determination of Orange II binding:

Amine group density was determined in accordance with a method by NOEL et al. (Bioconjugate Chemistry 22 (2011) 1690-1699) on PET fibers which were subjected to an aminolysis reaction beforehand. To this end, the weighed fiber samples were swirled in a dye solution (1.4 mg/ml Orange II in 1 mM HCl) (40° C., 30 min), rinsed three times in 1 mM HCl (RT, 10 min) in order to remove unbound dye, and then dried (10 min, 80° C.).

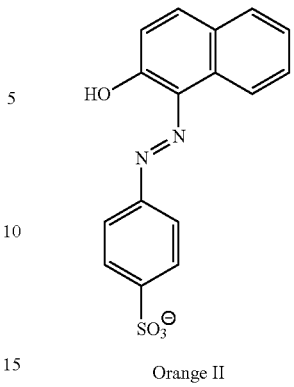

Orange II

Thereafter, the samples were swirled in diluted sodium hydroxide solution (20 mL, pH=12) (40° C., 30 min) in order to achieve a deprotonation of the amine groups and to elute the ionically bound dye molecules. After removal of the fibers, the solution was adjusted to pH=3 using hydrochloric acid (200 µL, 32%) and, if necessary, diluted using 1 mM hydrochloric acid.

From the solution thus obtained, the absorbance was determined at a wavelength of 484 nm. Since the molar extinction coefficient of the Orange II dye and the dilution factor are known, it is possible to deduce the amount of dye molecules in the solution. Since each protonated amine group is capable of binding one Orange II molecule under acidic conditions, the number of amine groups on the fiber sample can thus be indirectly deduced.

Determination of ionic capacity via acid-base titration:

To determine ionic capacity by means of acid-base titration, a (fiber) sample of known weight is packed in a dry state into a column and compressed to a density of 0.35 g/mL.

The titration comprises the following steps:
Equilibration and wetting with 10 mM KR buffer (pH=7, 15 bed volumes)
Complete protonation of the sulfonic acid groups by means of 5% HCl (20 bed volumes)
Rinsing with demineralized water (15 bed volumes)
Titration with 10 mM NaOH solution (20 bed volumes)
Rinsing with 10 mM KPi buffer (pH=7, 15 bed volumes)

During the titration, the conductivity signal at the column outlet is monitored. Since the dead volume of the column and system is known, it is possible to deduce the ionic capacity from the breakthrough curve of the 10 mM NaOH solution by means of integration, as will be explained with the aid of FIG. 1:

Since area $A_2$, which is accessible by means of a simple integration, is known, it is possible to deduce area $A_1$. The ionic binding capacity based on the fiber mass can be calculated as follows:

$$ion\text{-}binding\ capacity\left[\frac{mmol}{g}\right] = \frac{A_2\left[\frac{mS}{cm}\cdot L\right]\cdot 10\frac{mmol}{L}}{C_0\left[\frac{mS}{cm}\right]\cdot m_{Fibers}[g]}$$

Determination of Hydroxyl Group Density:

To determine hydroxyl group density, the substrate sample in question was reacted with sodium 3-bromopropanesulfonate. To this end, 0.5 g of substrate was incubated for 24 h in 5 mL of a solution consisting of 50.2% by weight of RO water, 29.8% by weight of a 32% by weight NaOH solution, and 20% by weight of sodium 3-bromopropanesulfonate. The fibers obtained were then washed with RO water.

The ionic capacity obtained was determined as described above by means of acid-base titration and, assuming a complete reaction, equated with the number of hydroxyl groups.

Determination of Initiator Density:

To determine the amount of immobilized initiator on the aminolysed samples, use was made of a method developed by KosioL (master's thesis by P. Kosiol, Georg-August-Universitat Gottingen, 2013).

Reagents:

Buffer: Sodium acetate (68 g) was dissolved in 200 mL of water and glacial acetic acid (30 mL) was added. The solution was topped up with water to 1 L. The pH was adjusted to 4.7.

Phenol Red solution: Phenol Red (120 mg) was dissolved in 200 mL of water. 0.1 M NaOH (12 mL) was added and the solution was topped up to 1 L.

Chloramine-T solution: Chloramine-T (0.15 g) was topped up to 100 mL. The solution was prepared fresh every day.

Sodium thiosulfate solution: Sodium thiosulfate (2.5 g) was topped up to 100 mL.

Calibration stock solution: Potassium bromide (74.5 mg) was topped up to 500 mL. The concentration of bromide was 0.01 g/L.

Calibration standards: By means of dilution with water, calibration standards of different concentrations were prepared from the stock solution according to the following pipetting scheme. From said standards, 5 mL were used further in each case.

TABLE 1

Pipetting scheme for the preparation of aqueous calibration standards

| Volume of the stock solution/μL | Final volume of the calibration standard/mL | Mass of bromide in 5 mL solution/μg |
|---|---|---|
| 200 | 10 | 10 |
| 400 | 10 | 20 |
| 800 | 10 | 40 |
| 1200 | 10 | 60 |
| 1600 | 10 | 80 |
| 2000 | 10 | 100 |

Performing a Calibration

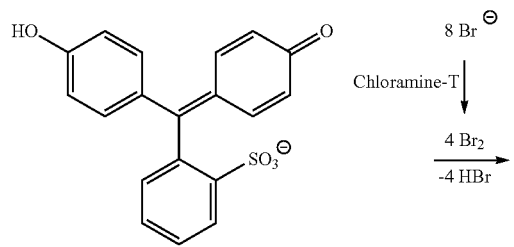

Phenol Red
$\lambda_{max}$ = 356 nm

-continued

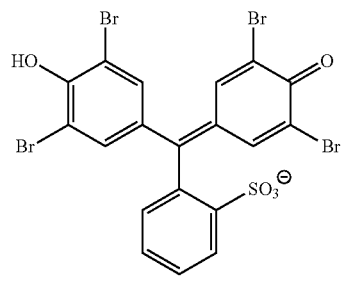

Bromophenol Blue
$\lambda_{max}$ = 589 nm

In a 10 mL volumetric flask, 5.00 mL of the calibration standard in question were admixed with 2.00 mL of buffer solution and 1.25 mL of Phenol Red solution. While shaking, 300 μL of chloramine-T solution were added. After exactly 1 min, 500 μL of thiosulfate solution were added. The solution was topped up to 10 mL. Via the resulting bromophenol blue, the absorbance was measured at 585 nm, which absorbance is linearly related to the concentration of bromophenol blue. The blank value used was a sample in which the same amount of water was added instead of the calibration standard. The calibration was carried out in duplicate with two sets of calibration standards.

Figure 2:
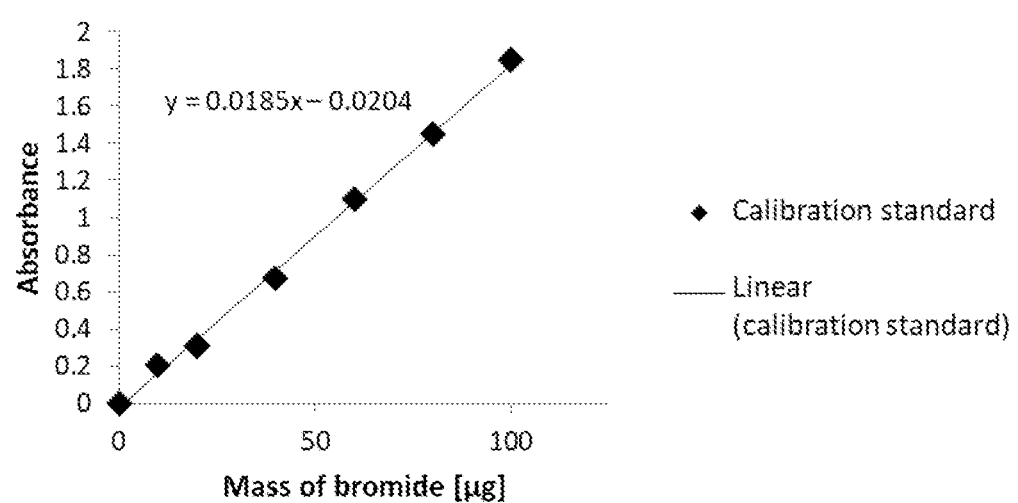
FIG. 2: Calibration curve for determining the amount of bromide in a sample.

By means of the calibration curve from FIG. 2, it was possible to establish the following relationship between the absorbance A and the mass of bromide $m_{Br^-}$ present in the sample:

$$m_{Br^-} [\mu g] = \left(\frac{A + 0.0204}{0.0185}\right)$$

Sample Preparation—Dehalogenation of an Immobilized Initiator

Figure 10:
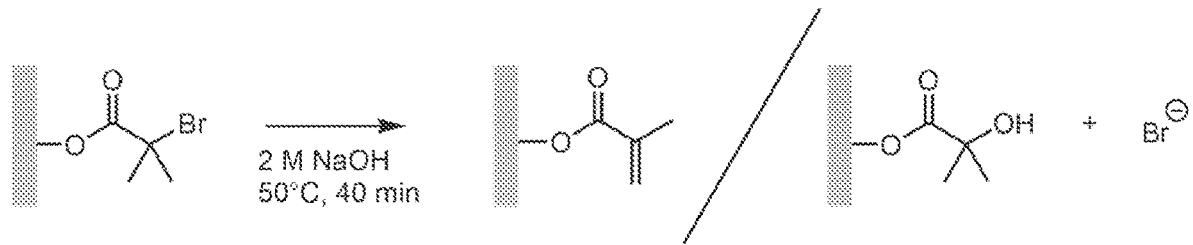
FIG. 10: Dehalogenation of an Immobilized Initiator

FIG. 10 illustrates the dehalogenation of an immobilized initiator. Samples provided with initiator were weighed. Thereafter, the samples were transferred to 25 mL laboratory bottles. 20 mL of 2 M sodium hydroxide solution were added in each case and the suspensions were stirred at 50° C. for 40 min. The selected reaction conditions allowed a quantitative dehalogenation of the initiator. The solutions were cooled to room temperature and filtered with the aid of syringe filters (0.20 μm). 10 mL of the solutions were in each case transferred to a 20 mL volumetric flask and in each case admixed with one drop of Phenol Red solution. The solutions were acidified with 1.5 M sulfuric acid up to a yellow color change. This was followed by topping up with water to 20 mL in order to obtain the prepared sample solutions.

To determine the amount of bromide in a sample of unknown bromide content, the dilutions displayed in Table 2 were prepared from each prepared sample solution. The dilutions were done in 10 mL volumetric flasks. Volumes of 5 mL were always set by pipetting sample solution and water. Thereafter, the diluted sample solutions were reacted analogously to the calibration standards and the absorbance values determined.

TABLE 2

Pipetting scheme for the preparation of diluted sample solutions

| # | Volume of the prepared sample solution/mL | Volume of water/mL | Final volume/mL | Dilution factor |
|---|---|---|---|---|
| 1 | 0.10 | 4.90 | 10 | 0.0025 |
| 2 | 0.25 | 4.75 | 10 | 0.00625 |
| 3 | 0.50 | 4.50 | 10 | 0.0125 |
| 4 | 1.0 | 4.00 | 10 | 0.025 |
| 5 | 2.0 | 3.00 | 10 | 0.05 |
| 6 | 5.0 | 0.00 | 10 | 0.125 |

Via the above formula, it was possible to calculate the mass of bromide in the sample. The total dilution factors for converting the mass of bromide to the entire membrane can be gathered from Table 2. Only the absorbance values could be further used, which values exhibited among one another a linear relationship with the respective dilution factors. Deviations from the linear behavior were caused, inter alia, by the ratio of the reagents used to the amounts of bromide not being constant. In the case of large amounts of bromide in the sample for example, the excess of molecular bromine formed with respect to the constant amount of Phenol Red led to a destruction of the tetrabromine compound to be detected. The resulting absorbance values deviated negatively from the linear behavior.

Descriptions of Syntheses:

Example 1: Modification of Polyester Fibers (PBT and PET) with Spacer Element Immobilization of Spacer:

In a typical reaction, a 10% by weight poly(allylamine) solution in RO water (70% v/v) and 1,4-dioxane (30% v/v) was adjusted to a pH of 12.5 using 32% by weight NaOH solution and admixed with a weighed amount of Winged Fibers (PBT) (Alasso Industries) or 4DG™ Fibers (PET) (Fiber Innovation Technology). 50 mL of poly(allylamine) solution (MW: 15 000 g/mol; Beckmann-Kenko GmbH) were used per gram of polyester fibers.

The suspension was stirred at 80° C. for 6 h. After reaching the desired reaction time, the fibers were filtered out and added to a large excess of RO water and stirred for 30 min. This was followed by filtering out again and washing with RO water until the filtrate no longer exhibits a basic pH. After drying at 60° C. for 6 h, the aminated fibers obtained were characterized with regard to loss of mass and to amine group density.

| Fiber type | Amine group density |
|---|---|
| Winged Fibers | $12 \pm 1.5$ $nm^{-2}$ |
| 4DG ™ | $18 \pm 4.5$ $nm^{-2}$ |

Immobilization of Initiator

In a typical immobilization, α-bromoisobutyryl bromide (1.00 mL, 1.86 g, 8.09 mmol) and triethylamine (1.50 mL, 1.08 g, 10.7 mmol) were added to 100 mL of anhydrous dichloromethane. 4 g of aminated fibers were suspended in this solution and shaken at room temperature for 2 h. For the work-up, 10 mL of isopropanol were slowly added drop by drop and shaking was carried out for a further 30 min. Thereafter, the fibers were filtered out and washed with water, isopropanol, acetone and again water. After drying at 40° C. for 12 h, the fibers provided with initiator were characterized with regard to the initiator density.

| Fiber type | Initiator density |
|---|---|
| Winged Fibers | $10.5 \pm 1.5$ $nm^{-2}$ |
| 4DG ™ | $15 \pm 4$ $nm^{-2}$ |

Spacer-Initiated Polymerization:

In a representative polymerization, glycidyl methacrylate (2.5 g, 17.5 mmol, 175 eq.) was dissolved in 100 mL of RO water and 100 mL of isopropanol. The solution was then degassed for 30 min by introduction of nitrogen. In the nitrogen counterstream, copper(I) bromide (15.0 mg, 104 μmol, 1.0 eq.), 2,2'-bipyridine (50.0 mg, 320 μmol, 3.1 eq.) and ascorbic acid (45.0 mg, 225 μmol, 1.25 eq.) were added and degassing was carried out for a further 30 min with stirring. In parallel, 1.0 g of fibers provided with initiator was degassed in a nitrogen stream. By means of a transfer cannula, the polymerization solution was added to the fibers under protective gas and stirring was carried out for 8 h with exclusion of oxygen. The polymerization was terminated by opening the reaction vessel and by introducing oxygen. The glycidyl methacrylate-modified fibers were washed with water and acetone in order to remove catalyst residues and polymer which is not bonded on the surface. The target product was obtained after drying at 40° C. for 6 h. The degree of grafting was determined gravimetrically in accordance with Equation (1).

| Fiber type | Degree of grafting |
|---|---|
| Winged Fibers | $6 \pm 1\%$ |
| 4DG ™ | $2 \pm 0.5\%$ |

Sulfonation of the Epoxide Groups:

The reaction to form a strong cation exchanger was carried out as follows:

600 g of water were initially charged and 180 g of $Na_2SO_3$, 20 g of $Na_2HPO_4 \cdot 2$ $H_2O$ and 50 g of TBABS (tetrabutylammonium bisulfate) were dissolved with cooling. The pH of the solution was adjusted to 8 using NaOH (32%) and water was added in steps until 1 kg of solution was reached. In the course of this, the pH was checked regularly and, in the event of a deviation, readjusted to pH 8 using NaOH (32%).

For the reaction, the amount of solution used was sufficient for all the fibers to be able to float freely in a 500 ml wide-neck screw-top bottle. The solution was heated to 85° C. and the fibers were reacted at 85° C. for 45 min with stirring.

| Support material | Ionic capacity |
|---|---|
| Winged Fibers | $220 \pm 25$ μmol/g |
| 4DG ™ | $60 \pm 10$ μmol/g |

Example 2: Modification of Polyester/Polyamide Nonwoven with Spacer Element

Immobilization of Spacer:

In a typical reaction, a 10% by weight poly(allylamine) solution in RO water (70% v/v) and 1,4-dioxane (30% v/v) was adjusted to a pH of 12.5 using 32% by weight NaOH solution and admixed with punched-out pieces (47 mm diameter) of a split-fiber nonwoven (Pluratexx2317 S, Freudenberg). 10 mL of poly(allylamine) solution (as described in Example 1) were used per punched-out piece.

The suspension was stirred at 80° C. for 6 h. After reaching the desired reaction time, the punched-out pieces were removed from the solution and added to a large excess of RO water and washed with RO water until the filtrate no longer exhibits a basic pH. After drying at 60° C. for 6 h, the aminated nonwoven materials obtained were characterized with regard to loss of mass and to amine group density.

| Support material | Amine group density |
|---|---|
| Split fiber PET/PA6 nonwoven | 9.0 nm$^{-2}$ |

(PET: polyethylene terephthalate; PA6: nylon 6)

Immobilization of Initiator:

In a typical immobilization, α-bromoisobutyryl bromide (1.00 mL, 1.86 g, 8.09 mmol) and triethylamine (1.50 mL, 1.08 g, 10.7 mmol) were added to 100 mL of anhydrous dichloromethane. 12 punched-out pieces (47 mm diameter) were suspended in said solution and shaken at room temperature for 2 h. For the work-up, 10 mL of isopropanol were slowly added drop by drop and shaking was carried out for a further 30 min. Thereafter, the punched-out pieces were removed and washed with water, isopropanol, acetone and again water. After drying at 40° C. for 12 h, the punched-out pieces provided with initiator were characterized with regard to the initiator density.

| Fiber type | Initiator density |
|---|---|
| Split fiber PET/PA6 nonwoven | 7.5 nm$^{-2}$ |

Spacer-Initiated Polymerization:

In a representative polymerization, glycidyl methacrylate (2.5 g, 17.5 mmol, 175 eq.) was dissolved in 100 mL of RO water and 100 mL of isopropanol. The solution was then degassed for 30 min by introduction of nitrogen. In the nitrogen counterstream, copper(I) bromide (15.0 mg, 104 µmol, 1.0 eq.), 2,2'-bipyridine (50.0 mg, 320 µmol, 3.1 eq.) and ascorbic acid (45.0 mg, 225 µmol, 1.25 eq.) were added and degassing was carried out for a further 30 min with stirring. In parallel, 4 punched-out pieces (47 mm diameter) were degassed in a nitrogen stream. By means of a transfer cannula, the polymerization solution was added to the fibers under protective gas and stirring was carried out for 16 h with exclusion of oxygen. The polymerization was terminated by opening the reaction vessel and by introducing oxygen. The glycidyl methacrylate-modified fibers were washed with water and acetone in order to remove catalyst residues and polymer which is not bonded on the surface. The target product was obtained after drying at 40° C. for 6 h. The degree of grafting was determined gravimetrically in accordance with Equation (1).

| Fiber type | Degree of grafting |
|---|---|
| Split fiber PET/PA6 nonwoven | 7% |

Sulfonation of the Epoxide Groups:

The reaction to form a strong cation exchanger was carried out as follows:

600 g of water were initially charged and 180 g of $Na_2SO_3$, 20 g of $Na_2HPO_4 \cdot 2\,H_2O$ and 50 g of TBABS were dissolved with cooling. The pH of the solution was adjusted to 8 using NaOH (32%) and water was added in steps until 1 kg of solution was reached. In the course of this, the pH was checked regularly and, in the event of a deviation, readjusted to pH 8 using NaOH (32%).

For the reaction, the amount of solution used was sufficient for all the punched-out pieces to be able to float freely in a 500 ml wide-neck screw-top bottle. The solution was heated to 85° C. and the punched-out pieces were reacted at 85° C. for 45 min with stirring.

| Support material | Ionic capacity |
|---|---|
| Split fiber PET/PA6 nonwoven | 2.70 µmol/cm$^2$ |

Example 3: Modification of Nylon Membrane with Spacer Element

Immobilization of Spacer:

In a typical reaction, a 10% by weight poly(allylamine) solution (as described in Example 1) in RO water (70% v/v) and 1,4-dioxane (30% v/v) was adjusted to a pH of 12.5 using 32% by weight NaOH solution and admixed with punched-out pieces (47 mm diameter) of a nylon membrane (type 21303, mean pore size 1.2 µm, Sartorius AG). 10 mL of poly(allylamine) solution were used per punched-out piece.

The suspension was stirred at 80° C. for 6 h. After reaching the desired reaction time, the punched-out pieces were removed from the solution and added to a large excess of RO water and washed with RO water until the filtrate no longer exhibits a basic pH. After drying at 60° C. for 6 h, the aminated nonwoven materials obtained were characterized with regard to loss of mass and to amine group density.

| Support material | Amine group density |
|---|---|
| Nylon membrane | 2.1 nm$^{-2}$ |

Immobilization of Initiator:

Punched-out pieces (47 mm) of a nylon membrane (type 21303) reacted with polyallylamine were immersed in a solution composed of dichloromethane (49.5 mL) and α-bromoisobutyryl bromide (500 NL) until they were completely wetted. The wetted punched-out pieces were incubated at room temperature for 5 min and then shaken in isopropanol for 30 min in order to terminate the reaction. This was followed by rinsing with RO water for 20 min and drying at 60° C. for 1 h.

Spacer-Initiated Polymerization:

In a representative polymerization, glycidyl methacrylate (2.5 g, 17.5 mmol, 175 eq.) was dissolved in 100 mL of RO water and 100 mL of isopropanol. The solution was then degassed for 30 min by introduction of nitrogen. In the nitrogen counterstream, copper(I) bromide (15.0 mg, 104 µmol, 1.0 eq.), 2,2'-bipyridine (50.0 mg, 320 µmol, 3.1 eq.) and ascorbic acid (45.0 mg, 225 µmol, 1.25 eq.) were added and degassing was carried out for a further 30 min with stirring. In parallel, 4 punched-out pieces (47 mm diameter) were degassed in a nitrogen stream. By means of a transfer cannula, the polymerization solution was added to the fibers under protective gas and stirring was carried out for 90 min with exclusion of oxygen. The polymerization was terminated by opening the reaction vessel and by introducing oxygen. The glycidyl methacrylate-modified fibers were washed with water and acetone in order to remove catalyst residues and polymer which is not bonded on the surface. The target product was obtained after drying at 40° C. for 6 h. The degree of grafting was determined gravimetrically in accordance with Equation (1).

| Fiber type | Degree of grafting |
| --- | --- |
| Nylon membrane | 2% |

Sulfonation of the Epoxide Groups:

The reaction to form a strong cation exchanger was carried out as follows:

600 g of water were initially charged and 180 g of $Na_2SO_3$, 20 g of $Na_2HPO_4 \cdot 2\,H_2O$ and 50 g of TBABS were dissolved with cooling. The pH of the solution was adjusted to 8 using NaOH (32%) and water was added in steps until 1 kg of solution was reached. In the course of this, the pH was checked regularly and, in the event of a deviation, readjusted to pH 8 using NaOH (32%).

For the reaction, the amount of solution used was sufficient for all the punched-out pieces to be able to float freely in a 500 ml wide-neck screw-top bottle. The solution was heated to 85° C. and the punched-out pieces were reacted at 85° C. for 45 min with stirring.

| Support material | Ionic capacity |
| --- | --- |
| Nylon membrane | $0.3 \pm 0.02\ \mu mol/cm^2$ |

Example 4: Modification of PBT Fibers with Spacer Element

Immobilization of Spacer:

In a typical reaction, Winged Fibers (PBT) were shaken at room temperature for 1 h in a solution consisting of 30% by weight of 1,4-butanediol diglycidyl ether (BuDGE) and 70% by weight of 0.15 M KOH solution. The fibers were filtered out and washed with ethanol and RO water. The epoxy-activated fibers obtained were then reacted at 80° C. for 16 h in a solution composed of 2% by weight of polyvinyl alcohol (PVA, Mw=9000–10 000) in 0.15 M KOH solution. The fibers were then filtered out and washed with ethanol and RO water and dried at 40° C. for 12 h.

| Fiber type | Hydroxyl group density |
| --- | --- |
| Winged Fibers | $18.3\ nm^{-2}$ |

Immobilization of Initiator:

In a typical immobilization, α-bromoisobutyryl bromide (1.00 mL, 1.86 g, 8.09 mmol) and triethylamine (1.50 mL, 1.08 g, 10.7 mmol) were added to 100 mL of anhydrous dichloromethane. 4 g of PVA-modified fibers were suspended in this solution and shaken at room temperature for 2 h. For the work-up, 10 mL of isopropanol were slowly added drop by drop and shaking was carried out for a further 30 min. Thereafter, the fibers were filtered out and washed with water, isopropanol, acetone and again water. After drying at 40° C. for 12 h, the fibers provided with initiator were characterized with regard to the initiator density.

| Fiber type | Initiator density |
| --- | --- |
| Winged Fibers | $15.6\ nm^{-2}$ |

Spacer-Initiated Polymerization:

In a representative polymerization, glycidyl methacrylate (2.5 g, 17.5 mmol, 175 eq.) was dissolved in 100 mL of RO water and 100 mL of isopropanol. The solution was then degassed for 30 min by introduction of nitrogen. In the nitrogen counterstream, copper(I) bromide (15.0 mg, 104 µmol, 1.0 eq.), 2,2'-bipyridine (50.0 mg, 320 µmol, 3.1 eq.) and ascorbic acid (45.0 mg, 225 µmol, 1.25 eq.) were added and degassing was carried out for a further 30 min with stirring. In parallel, 1.0 g of fibers provided with initiator was degassed in a nitrogen stream. By means of a transfer cannula, the polymerization solution was added to the fibers under protective gas and stirring was carried out for 5 h with exclusion of oxygen. The polymerization was terminated by opening the reaction vessel and by introducing oxygen. The glycidyl methacrylate-modified fibers were washed with water and acetone in order to remove catalyst residues and polymer which is not bonded on the surface. The target product was obtained after drying at 40° C. for 6 h. The degree of grafting was determined gravimetrically in accordance with Equation (1).

| Fiber type | Degree of grafting |
| --- | --- |
| Winged Fibers | 8% |

Sulfonation of the Epoxide Groups:

The reaction to form a strong cation exchanger was carried out as follows:

600 g of water were initially charged and 180 g of $Na_2SO_3$, 20 g of $Na_2HPO_4 \cdot 2\,H_2O$ and 50 g of TBABS were dissolved with cooling. The pH of the solution was adjusted to 8 using NaOH (32%) and water was added in steps until 1 kg of solution was reached. In the course of this, the pH was checked regularly and, in the event of a deviation, readjusted to pH 8 using NaOH (32%).

For the reaction, the amount of solution used was sufficient for all the fibers to be able to float freely in a 500 ml wide-neck screw-top bottle. The solution was heated to 85° C. and the fibers were reacted at 85° C. for 45 min with stirring.

| Support material | Ionic capacity |
| --- | --- |
| Winged Fibers | 280 μmol/g |

Binding for lysozyme was 305 mg/g, and for IgG it was 278 mg/g.

Comparative Example 1: ATRP without Spacer on Cellulose Membrane

Immobilization of Initiator:

Punched-out pieces (60 mm) of a crosslinked regenerated cellulose membrane (10242) were immersed in a solution composed of dichloromethane (49.5 mL) and α-bromoisobutyryl bromide (500 μL) until they were completely wetted. The wetted punched-out pieces were incubated at room temperature for 5 min and then shaken in isopropanol for 30 min in order to terminate the reaction. This was followed by rinsing with RO water for 20 min and drying at 60° C. for 1 h.

| Initiator density |
| --- |
| 10.6 nm$^{-2}$ |

Surface-initiated polymerization:

In a representative polymerization, glycidyl methacrylate (2.5 g, 17.5 mmol, 175 eq.) was dissolved in 100 mL of RO water and 100 mL of isopropanol. The solution was then degassed for 30 min by introduction of nitrogen. In the nitrogen counterstream, copper(I) bromide (15.0 mg, 104 μmol, 1.0 eq.), 2,2'-bipyridine (50.0 mg, 320 μmol, 3.1 eq.) and ascorbic acid (45.0 mg, 225 μmol, 1.25 eq.) were added and degassing was carried out for a further 30 min with stirring. In parallel, 5 punched-out pieces (60 mm) of the membrane provided with initiator were degassed in a nitrogen stream. By means of a transfer cannula, the polymerization solution was added to the punched-out pieces under protective gas and stirring was carried out for 8 h with exclusion of oxygen. The polymerization was terminated by opening the reaction vessel and by introducing oxygen. The glycidyl methacrylate-modified punched-out pieces were washed with water and acetone in order to remove catalyst residues and polymer which is not bonded on the surface. The target product was obtained after drying at 40° C. for 6 h. The degree of grafting was determined gravimetrically in accordance with Equation (1).

| Degree of grafting |
| --- |
| 10 ± 1% |

Sulfonation of the Epoxide Groups:

The reaction to form a strong cation exchanger was carried out as follows:

600 g of water were initially charged and 180 g of Na$_2$SO$_3$, 20 g of Na$_2$HPO$_4$·2 H$_2$O and 50 g of TBABS were dissolved with cooling. The pH of the solution was adjusted to 8 using NaOH (32%) and water was added in steps until 1 kg of solution was reached. In the course of this, the pH was checked regularly and, in the event of a deviation, readjusted to pH 8 using NaOH (32%).

For the reaction, the amount of solution used was sufficient for all the membranes to be able to float freely in a 500 ml wide-neck screw-top bottle. The solution was heated to 85° C. and the membranes were reacted at 85° C. for 45 min with stirring.

| Ionic capacity |
| --- |
| 4.00 μmol/cm$^2$ |

Comparative Example 2: ATRP without Spacer on Fibers

Surface Activation without Spacer:

In a typical reaction, 5 g of fibers (Winged Fibers (PBT) or 4DG™ Fibers (PET)) were stirred in a solution composed of 50 mL of ethylenediamine and 50 mL of ethanol at 50° C. for 2 h. After reaching the desired reaction time, the fibers were filtered out, added to a large excess of RO water and stirred for 30 min. This was followed by filtering out again and washing with RO water until the filtrate no longer exhibits a basic pH. After drying at 60° C. for 6 h, the aminated fibers obtained were characterized with regard to loss of mass and to amine group density.

| Fiber type | Amine group density |
| --- | --- |
| Winged Fibers | 4.5 nm$^{-2}$ |

Immobilization of Initiator:

In a typical immobilization, α-bromoisobutyryl bromide (1.00 mL, 1.86 g, 8.09 mmol) and triethylamine (1.50 mL, 1.08 g, 10.7 mmol) were added to 100 mL of anhydrous dichloromethane. 4 g of aminated fibers were suspended in this solution and shaken at room temperature for 2 h. For the work-up, 10 mL of isopropanol were slowly added drop by drop and shaking was carried out for a further 30 min. Thereafter, the fibers were filtered out and washed with water, isopropanol, acetone and again water. After drying at 40° C. for 12 h, the fibers provided with initiator were characterized with regard to the initiator density.

| Fiber type | Initiator density |
| --- | --- |
| Winged Fibers | 3.6 nm$^{-2}$ |

Surface-Initiated Polymerization:

In a representative polymerization, glycidyl methacrylate (2.5 g, 17.5 mmol, 175 eq.) was dissolved in 100 mL of RO water and 100 mL of isopropanol. The solution was then degassed for 30 min by introduction of nitrogen. In the nitrogen counterstream, copper(I) bromide (15.0 mg, 104 μmol, 1.0 eq.), 2,2'-bipyridine (50.0 mg, 320 μmol, 3.1 eq.) and ascorbic acid (45.0 mg, 225 μmol, 1.25 eq.) were added and degassing was carried out for a further 30 min with stirring. In parallel, 1.0 g of fibers provided with initiator was degassed in a nitrogen stream. By means of a transfer cannula, the polymerization solution was added to the fibers under protective gas and stirring was carried out for 8 h with exclusion of oxygen. The polymerization was terminated by opening the reaction vessel and by introducing oxygen. The glycidyl methacrylate-modified fibers were washed with water and acetone in order to remove catalyst residues and polymer which is not bonded on the surface. The target product was obtained after drying at 40° C. for 6 h. The degree of grafting was determined gravimetrically in accordance with Equation (1).

| Fiber type | Degree of grafting |
|---|---|
| Winged Fibers | 2 ± 0.5% |

Sulfonation of the Epoxide Groups:

The reaction to form a strong cation exchanger was carried out as follows:

600 g of water were initially charged and 180 g of Na$_2$SO$_3$, 20 g of Na$_2$HPO$_4$·2 H$_2$O and 50 g of TBABS were dissolved with cooling. The pH of the solution was using NaOH was reached. In the course of this, the pH was checked regularly and, in the event of a deviation, readjusted to pH 8 using NaOH (32%).

For the reaction, the amount of solution used was sufficient for all the fibers to be able to float freely in a 500 ml wide-neck screw-top bottle. The solution was heated to 85° C. and the fibers were reacted at 85° C. for 45 min with stirring.

| Fiber type | Ionic capacity |
|---|---|
| Winged Fibers | 100 ± 10 µmol/g |

Comparative Example 3: ATRP without Spacer on Nylon Membrane

Surface Activation without Spacer:

In a typical reaction, punched-out pieces (47 mm diameter) of a nylon membrane (type 21303) were shaken at room temperature for 10 min in a solution consisting of 0.5% by weight of chloramine-T, 95.5% by weight of RO water and 4% by weight of sodium acetate buffer (1 M, pH=6). After the reaction, the membranes were washed in RO water for 10 min and dried at 60° C. for 1 h.

Surface-Initiated Polymerization:

In a representative polymerization, glycidyl methacrylate (2.5 g, 17.5 mmol, 175 eq.) was dissolved in 100 mL of RO water and 100 mL of isopropanol. The solution was then degassed for 30 min by introduction of nitrogen. In the nitrogen counterstream, copper(I) bromide (15.0 mg, 104 µmol, 1.0 eq.), 2,2'-bipyridine (50.0 mg, 320 µmol, 3.1 eq.) and ascorbic acid (45.0 mg, 225 µmol, 1.25 eq.) were added and degassing was carried out for a further 30 min with stirring. In parallel, 3 punched-out pieces (47 mm diameter) were degassed in a nitrogen stream. By means of a transfer cannula, the polymerization solution was added to the punched-out pieces under protective gas and stirring was carried out for 90 min with exclusion of oxygen. The polymerization was terminated by opening the reaction vessel and by introducing oxygen. The glycidyl methacrylate-modified punched-out pieces were washed with water and acetone in order to remove catalyst residues and polymer which is not bonded on the surface. The target product was obtained after drying at 40° C. for 6 h. The degree of grafting was determined gravimetrically in accordance with Equation (1).

| Fiber type | Degree of grafting |
|---|---|
| Nylon membrane | 9% |

Sulfonation of the Epoxide Groups:

The reaction to form a strong cation exchanger was carried out as follows:

600 g of water were initially charged and 180 g of Na$_2$SO$_3$, 20 g of Na$_2$HPO$_4$·2 H$_2$O and 50 g of TBABS were dissolved with cooling. The pH of the solution was adjusted to 8 using NaOH (32%) and water was added in steps until 1 kg of solution was reached. In the course of this, the pH was checked regularly and, in the event of a deviation, readjusted to pH 8 using NaOH (32%).

For the reaction, the amount of solution used was sufficient for all the punched-out pieces to be able to float freely in a 500 ml wide-neck screw-top bottle. The solution was heated to 85° C. and the punched-out pieces were reacted at 85° C. for 45 min with stirring.

| Support material | Ionic capacity |
|---|---|
| Nylon membrane | 2.5 ± 0.2 µmol/cm$^2$ |

Comparison between inventive and conventional adsorption media:

The above-synthesized inventive adsorption media were compared with commercially available adsorption media and the above-synthesized (noninventive) comparison adsorption media with regard to the ratio between static protein binding and ionic capacity for lyosyme and IgG.

The inventive adsorption media based on PBT exhibit, owing to the presence of a flexible spacer element, 1.5- to 3.6-fold increased values for the ratio between static protein-binding capacity and ionic binding capacity for lysozyme in comparison with chromatography matrices without said spacer element. In the case of immunoglobulin (IgG), the aforementioned ratio for the inventive adsorption media is increased by a factor of from 1.7 to 3.7 (see Table 3 for inventive adsorption media comprising PBT).

A similar result emerges for inventive adsorption media based on PET: owing to the presence of a flexible spacer element, the result is 1.2- to 2.8-fold increased values for the ratio between static protein-binding capacity and ionic binding capacity for lysozyme in comparison with chromatography matrices without said spacer element. In the case of immunoglobulin (IgG), the aforementioned ratio for the inventive adsorption media is increased by a factor of from 1.4 to 3 (see Table 4 for inventive adsorption media comprising PET).

Table 5 likewise demonstrates that, in the case of the nylon membrane embodiment, chromatography media containing spacer elements have a 1.5- to 4.5-fold increased ratio between static protein-binding capacity and ionic capacity in comparison with media without spacer element, and the increase in said ratio for the split-fiber nonwoven is within a comparable range of a 1.5- to 4-fold increase.

These findings demonstrate that, in the case of the inventive adsorption media, high binding capacities for proteins can be achieved even at a low ligand density.

linking and owing to the flexible polymeric spacer elements. This results in a large value for the ratio between static protein-binding capacity and ionic capacity, as has been

TABLE 3

| Comparison parameter | Sartobind S[5] | Fractogel EMD[6] $SO_3^-$ (M)[1] | ATRP without spacer Winged Fibers (PBT) | ATRP with PAA spacer Winged Fibers (PBT) |
|---|---|---|---|---|
| Static protein binding/ionic capacity ratio for lysozyme and IgG [mg/µmol] | 0.33 ± 0.05 lysozyme[2] 0.30 ± 0.02 IgG[3] | 0.77 ± 0.1 lysozyme[2] 0.66 ± 0.08 IgG[4] | 0.71 ± 0.12 lysozyme[2] 0.62 ± 0.1 IgG[3] | 1.19 ± 0.06 lysozyme[2] 1.11 ± 0.07 IgG[3] |

PBT: polybutylene terephthalate;
PAA: polyallylamine
[1]E. Grushka, N. Grinberg, *Advances in Chromatography*, Vol. 47, 2009 and EP 2 153 877 A1
[2]KPi buffer 10 mM, pH = 7, conductivity = 1.75 mS/cm
[3]Sodium acetate buffer 10 mM, pH = 5, 100 mM NaCl
[4]Sodium acetate buffer 10 mM, pH = 5
[5]Nonwoven-reinforced regenerated crosslinked cellulose membrane containing sulfonic acid ligands
[6]Consisting of crosslinked methacrylates; Merck

TABLE 4

| Comparison parameter | Sartobind S[5] | Fractogel EMD[6] $SO_3^-$ (M)[1] | ATRP without spacer 4DG ™ Fibers (PET) | ATRP with PAA spacer 4DG ™ Fibers (PET) |
|---|---|---|---|---|
| Static protein binding/ionic capacity ratio for lysozyme and IgG [mg/µmol] | 0.33 ± 0.05 lysozyme[2] 0.30 ± 0.02 IgG[3] | 0.77 ± 0.1 lysozyme[2] 0.66 ± 0.08 IgG[4] | 0.61 lysozyme[2] 0.57 IgG[3] | 0.91 ± 0.12 lysozyme[2] 0.90 ± 0.08 IgG[3] |

PET: polyethylene terephthalate;
PAA: polyallylamine
[1]E. Grushka, N. Grinberg, *Advances in Chromatography*, Vol. 47, 2009 and EP 2 153 877 A1
[2]KPi buffer 10 mM, pH = 7, conductivity = 1.75 mS/cm
[3]Sodium acetate buffer 10 mM, pH = 5, 100 mM NaCl
[4]Sodium acetate buffer 10 mM, pH = 5
[5]Nonwoven-reinforced regenerated crosslinked cellulose membrane containing sulfonic acid ligands
[6]Consisting of crosslinked methacrylates; Merck

TABLE 5

| Comparison parameter | Sartobind S[5] | Fractogel EMD[6] $SO_3^-$ (M)[1] | ATRP without spacer Nylon membrane | ATRP with PAA spacer Nylon membrane | ATRP with PAA spacer on split-fiber nonwoven |
|---|---|---|---|---|---|
| Static protein binding/ionic capacity ratio for lysozyme and IgG [mg/µmol] | 0.33 ± 0.05 lysozyme[2] 0.30 ± 0.02 IgG[3] | 0.77 ± 0.1 lysozyme[2] 0.66 ± 0.08 IgG[3] | 0.30 ± 0.12 lysozyme[2] 0.22 ± 0.05 IgG[4] | 1.12 ± 0.08 lysozyme[2] 0.99 ± 0.09 IgG[3] | 1.19 ± 0.09 lysozyme[2] 1.01 ± 0.09 IgG[3] |

PAA: polyallylamine
[1]E. Grushka, N. Grinberg, *Advances in Chromatography*, Vol. 47, 2009 and EP 2 153 877 A1
[2]KPi buffer 10 mM, pH = 7, conductivity = 1.75 mS/cm
[3]Sodium acetate buffer 10 mM, pH = 5, 100 mM NaCl
[4]Sodium acetate buffer 10 mM, pH = 5
[5]Nonwoven-reinforced regenerated crosslinked cellulose membrane containing sulfonic acid ligands
[6]Consisting of crosslinked methacrylates; Merck Dependency of Permeability on the Structure of the Polymer Chains Containing Ligands Inter alia, it is an object of the present invention to provide an adsorption medium in which the chromatographically active centers (ligands) can be optimally utilized as binding sites, meaning that the number of ligands in the adsorption medium can be reduced. According to the invention, this is achieved by the polymer chains containing ligands having a high level of flexibility owing to their low level of crossshown above. In this way, the number of ionic ligands can be reduced to a very large extent. The result is:
  low demand for ligand during production;
  optimization of permeability due to relatively low swelling of the graft polymer.

To illustrate the influence of the polymer chains containing ligands on permeability, membranes composed of regenerated, crosslinked cellulose were modified by means of ATRP without spacer and reacted to form strong anion exchangers and, at the same time, chain density, chain length and ligand density were varied.

Chain Length:

While keeping chain density the same, the chain length was varied by means of different polymerization times. The permeability of the adsorption medium was determined as a function of the chain length (see FIG. 3).

Figure 3:
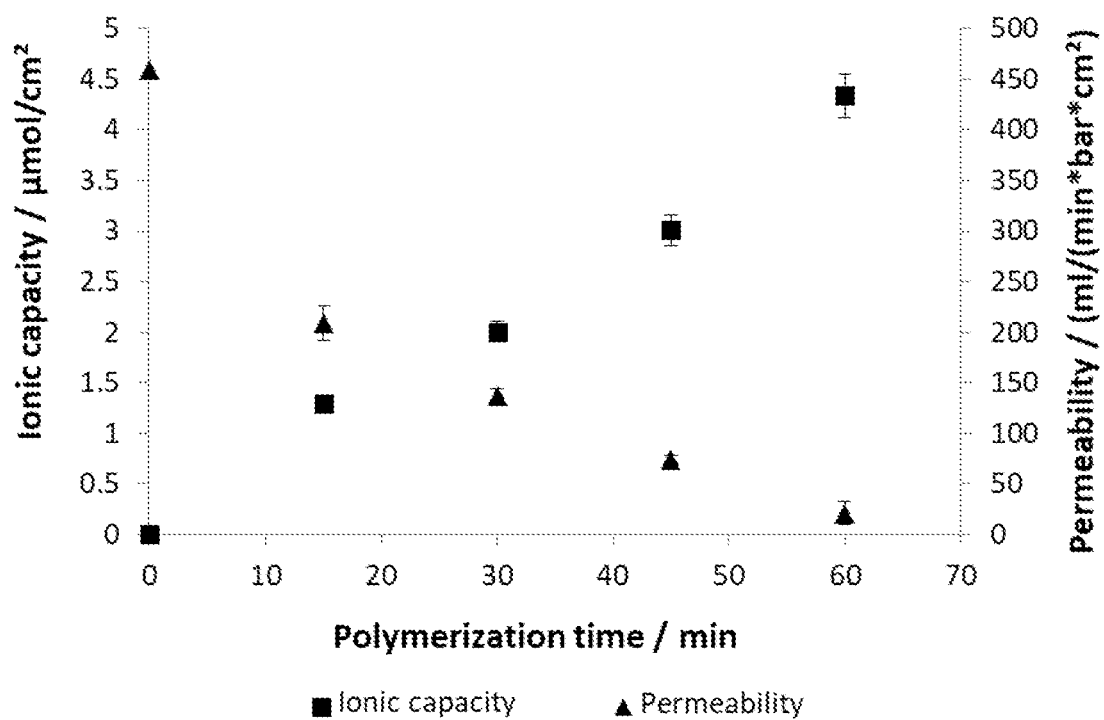
FIG. 3: Permeability as a function of chain length.

As is evident from FIG. 3, the permeability drops with rising chain length and thus higher ligand number. Advantageously, it is thus possible by means of the present invention, in which there is a relatively low demand for ligands owing to the optimal utilization of the ligands as binding sites, to avoid a reduction in the permeability of the adsorption medium.

Chain Density:

It was possible to vary the chain density by means of differing density of the surface-bonded ATRP initiator. While keeping polymer chain length the same, the permeability of the membrane was determined as a function of the determined initiator density (see FIG. 4).

Figure 4:
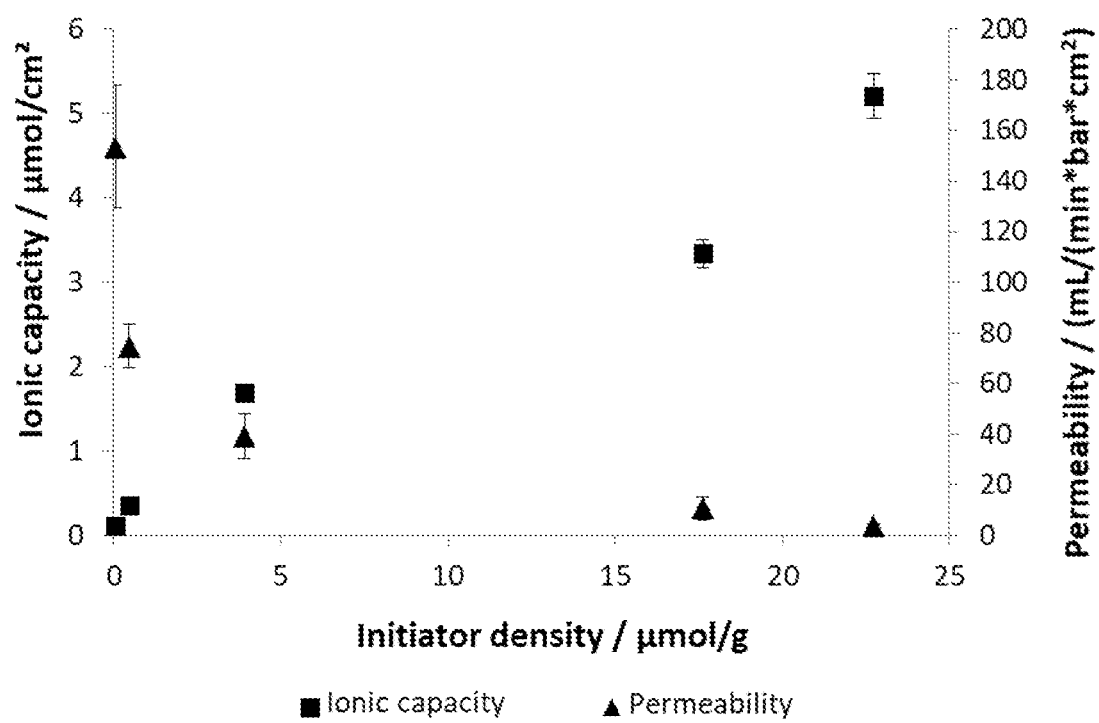
FIG. 4: Permeability as a function of initiator density.

As is evident from FIG. 4, the permeability drops with rising chain density and thus higher ligand number. Advantageously, it is thus possible by means of the present invention, in which there is a relatively low demand for polymer chains containing ligands owing to the optimal utilization of the ligands as binding sites, to avoid a reduction in the permeability of the adsorption medium.

Ligand Density:

While keeping polymer chain length and density the same, the ligand density in the hydrogel was varied by copolymerization of 2-(methacryloyloxy)ethyltrimethylammonium chloride with nonionic or inert monomers, such as hydroxyethyl methacrylate (HEMA). The permeability of the membrane was determined as a function of the ionic capacity obtained (see FIG. 5).

Figure 5:
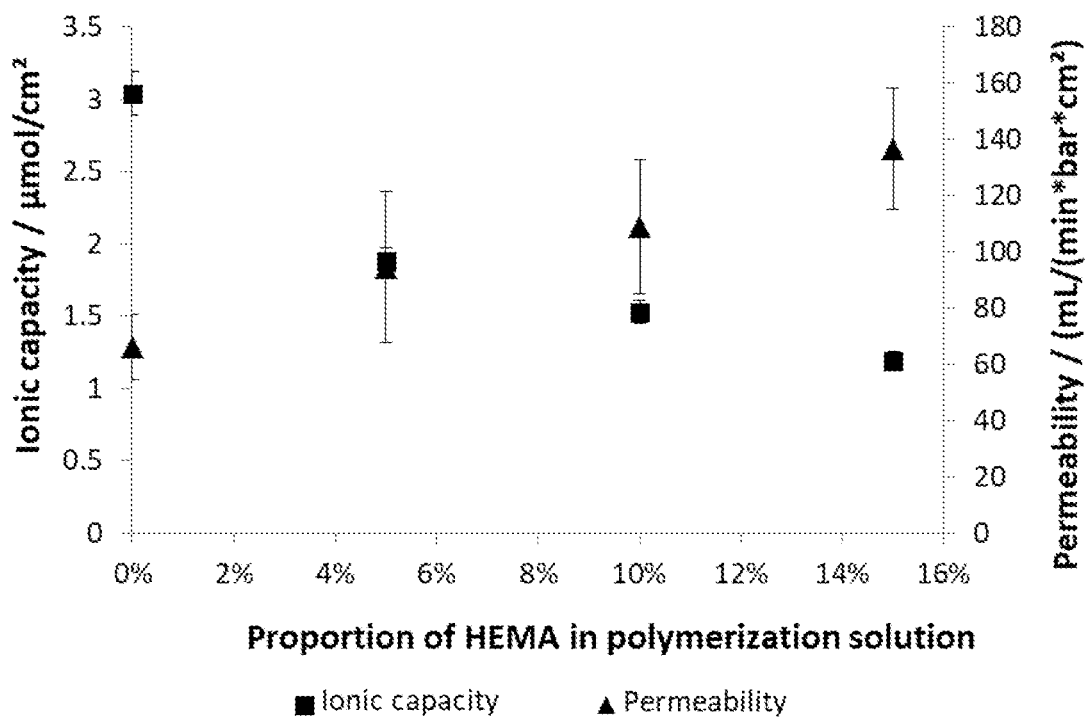
FIG. 5: Permeability as a function of ligand density.

As is evident from FIG. 5, a reduction in the ionic functionalities while keeping chain length and density the same leads to an increase in permeability.

In summary, it can therefore be stated that, in general, an increase in ionic functionalities within the polymer chains, caused by relatively high chain length and density or relatively high ligand density along the polymer chains, leads to a decrease in permeability. The present invention therefore advantageously provides an adsorption medium which allows an optimal utilization of the ligand sites and achieves high binding capacities for proteins at lowest possible ligand density.

Figure 6:
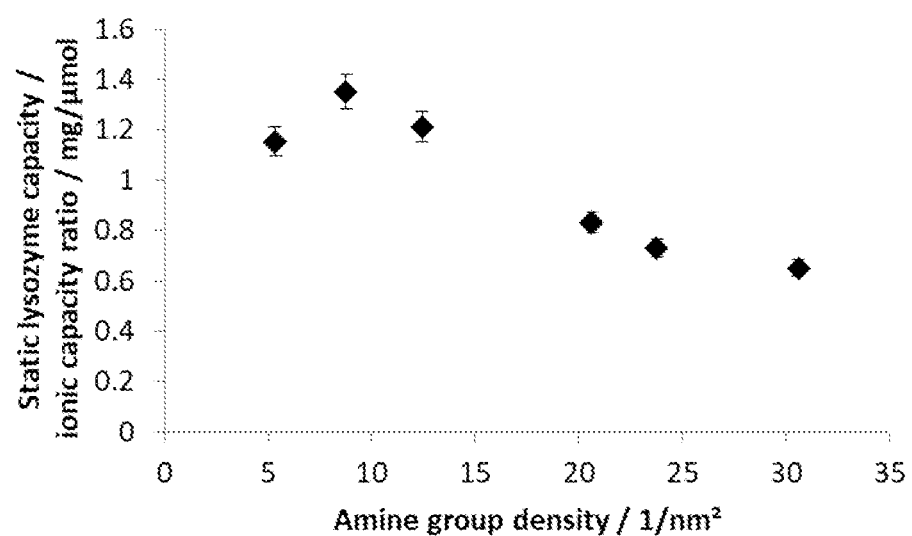
FIG. 6: Dependence of the ratio of static lysozyme-binding capacity to ionic capacity on the amine group density.

Influence of chain density on the accessibility of the polymer chains containing ligands:

As already shown, modified Winged Fibers exhibit a significantly higher ratio of static protein-binding capacity to ionic capacity than membranes having a comparable initiator density. In the tested range, the chain density does not appear to have any significant influence on the available binding volume. However, further tests for distinctly longer aminolysis times and, as a result, higher amine group densities or initiator/chain densities exhibit a profile similar to the membrane model. It can be observed that, even in the case of achieved chain densities that are very high, significantly more free binding volume is available. In the case of short aminolysis times and thus lower chain densities, a plateau can be observed. The ratio of static protein binding to ionic capacity assumes a virtually constant value (see FIG. 6).

Thus, an optimal range from 0.1 to 30 $nm^{-2}$ for amine group densities or initiator densities can be determined.

Crosslinking of the polymer layer containing ligands of a strong anion exchanger by means of bifunctional monomers:

In general, crosslinking of the polymer chains containing ligands can be controlled by copolymerization of monofunctional and bifunctional monomers. The proportion of the crosslinker (bifunctional monomer) allows direct control of the degree of crosslinking and, when the copolymerization parameters are known, quantification too.

Figure 7:
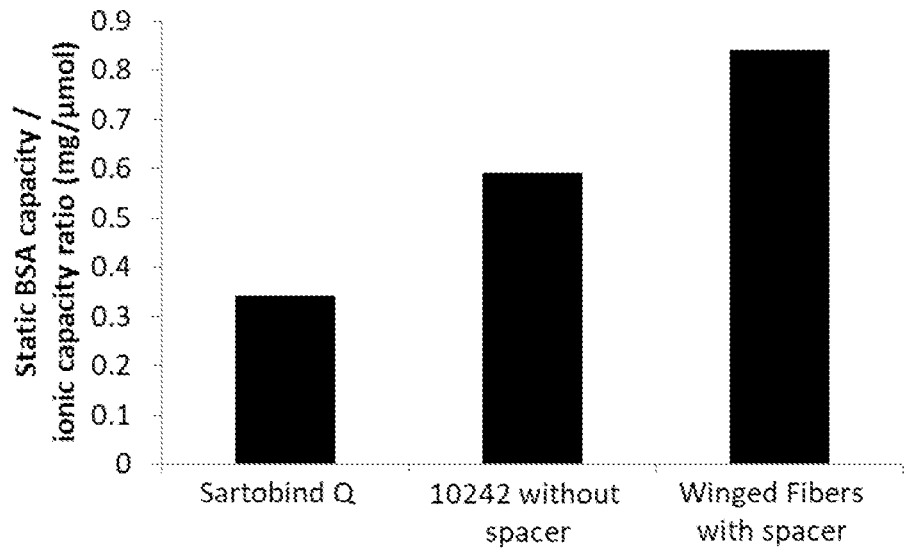
FIG. 7: Ratio of static protein-binding capacity to ionic capacity.

Strong anion-exchange materials were produced by carrying out an SI-ATRP (surface-initiated atom transfer radical polymerization) of the monomers 2-(methacryloyloxy)ethyltrimethylammonium chloride (METAC) and methylenebisacrylamide on different support materials. The ratio of protein-binding capacity to ionic capacity was determined in accordance with known methods. The results for a polymerization without crosslinker within the hydrogel layer are shown in FIG. 7. Included as comparative value is the value for Sartobind® Q as example of an uncontrolled radical polymerization with comparable ligand chemistry. Binding was determined with respect to BSA in TRIS/HCl buffer (pH=7.2, conductivity=1.8 mS/cm) as model protein.

Figure 8:
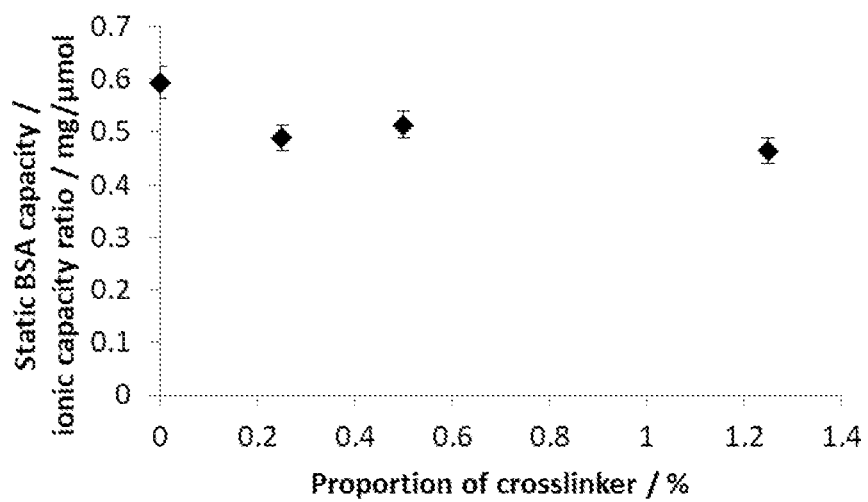
FIG. 8: Ratio of static protein-binding capacity to ionic capacity on a regenerated, crosslinked cellulose membrane.
Figure 9:
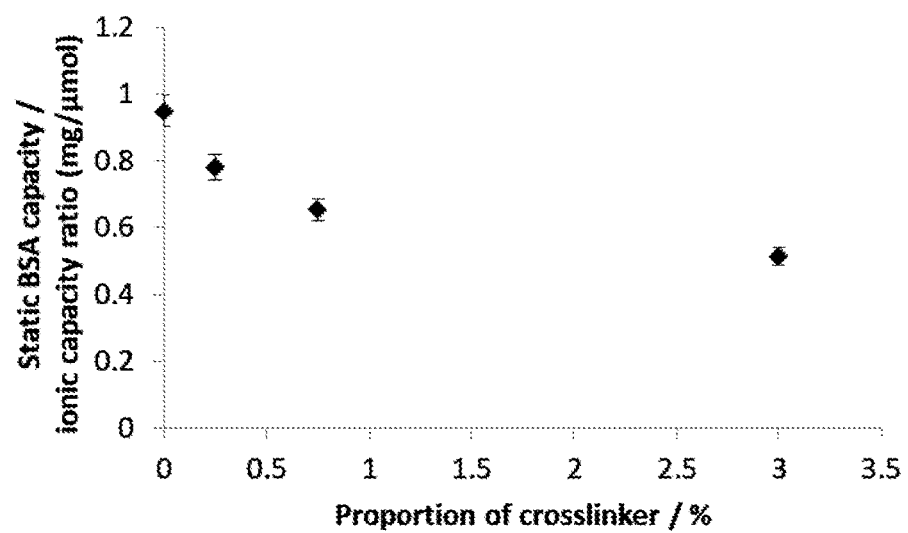
FIG. 9: Ratio of static protein-binding capacity to ionic capacity on "PBT Winged Fibers" containing a polyallylamine spacer.

On both model systems ("Winged Fibers" with spacer and cellulose membrane without spacer), a controlled crosslinking of the polymer chains containing ligands was achieved by addition of various proportions of methylenebisacrylamide. The influence on the ratio of static protein capacity to ionic capacity is shown in FIGS. 8 and 9.

For both support media, a distinct decrease in ligand accessibility can be observed. Said decrease is distinctly stronger for a polymerization with spacer. These observations show that the degree of crosslinking is directly related to ligand accessibility and that a limit should preferably not be exceeded for the polymer chains containing ligands.

The invention claimed is:

1. An adsorption medium comprising
   a chromatography matrix having a surface, the chromatography matrix selected from the group consisting of natural or synthetic fibers, polymer membranes, nonwovens and wovens;
   polymeric spacer elements having a molecular weight per polymeric spacer element ranging from 5000 to 2,000,000 g/mol, wherein the polymeric spacer elements are selected from the group consisting of polyamines and polyvinyl alcohols, and wherein the polymeric spacer elements are directly chemically or physically bonded to the surface of the chromatography matrix; and
   poly(meth)acrylate polymer chains containing chromatographically active centers, wherein the chromatographically active centers are selected from the group consisting of anionic and cationic groups and wherein the poly(meth)acrylate polymer chains are chemically bonded to the polymeric spacer elements.

2. The adsorption medium as claimed in claim 1, wherein the polymeric spacer elements do not have epoxy groups.

3. The adsorption medium as claimed in claim 1, wherein the adsorption medium has a degree of grafting ranging from 1% to 50%.

4. The adsorption medium as claimed in claim 1, wherein the chromatography matrix has a functional group density ranging from 1.5 to 30 $nm^{-2}$.

5. The adsorption medium as claimed in claim 1, wherein the natural or synthetic fibers are selected from the group consisting of polyethylene terephthalate (PET), cellulose, cellulose derivatives, nylon, polyethylene (PE), polyamide (PA), polyethersulfone (PES), polyvinylidene difluoride (PVDF), polytetrafluoroethylene (PTFE), polypropylene (PP), and polysulfone.

6. The adsorption medium as claimed in claim 1, wherein the polymer membranes are selected from the group consisting of cellulose, cellulose derivatives, nylon, polyester, polyethylene (PE), polyamide (PA), polyethersulfone (PES), polyvinylidene difluoride (PVDF), polytetrafluoroethylene (PTFE), polypropylene (PP), and polysulfone.

7. The adsorption medium as claimed in claim 1, wherein the wovens are selected from the group consisting of cellulose, cellulose derivatives, nylon, polyester, polyethylene (PE), polyamide (PA), polyethersulfone (PES), polyvinylidene difluoride (PVDF), polytetrafluoroethylene (PTFE), polypropylene (PP), and polysulfone.

8. The adsorption medium as claimed in claim 1, wherein the nonwovens are selected from the group consisting of cellulose, cellulose derivatives, nylon, polyester, polyethylene (PE), polyamide (PA), polyethersulfone (PES), polyvinylidene difluoride (PVDF), polytetrafluoroethylene (PTFE), polypropylene (PP), and polysulfone.

9. The adsorption medium as claimed in claim 1, wherein the polyamine spacer elements are selected from the group consisting of polyallylarnine, polyvinylamine, polyethyleneirnine, poly(4-aminostyrene), chitosan, poly(N-methylvinylamine), poly(N-methylallylamine), poly(N,N-dimethylvinylamine), poly(N,N-dimethyliallylamine), and poly(oleylamines).

10. The adsorption medium as claimed in claim 1, wherein the poly(meth)acrylate polymer chains are selected from the group consisting of poly(1-glycerol (meth)acrylate), poly(2-glycerol (meth)acrylate), poly(hydroxy-ethyl (meth)acrylate), poly(hydroxypropyl (meth)acrylate), poly(2-aminoethyl (meth)acrylate), poly(2-aminopropyl (meth)acrylate), poly(2-(diethylamino)ethyl (meth)acrylate), polyethylene glycol (meth)acrylate), poly(hydroxybutyl (meth)acrylate), poly(glycosyloxyethyl (meth)acrylate), poly(3-(acryloyloxy)-2-hydroxypropyl (meth)acrylate), poly(3-chloro-2-hydroxypropyl (meth)acrylate), poly([tris(hydroxymethyl)] (meth)acrylate), poly(2-(4-benzoyl-3-hydroxyphenoxy)ethyl (meth)acrylates) and poly(glycidylmethacrylate).

11. The adsorption medium as claimed in claim 1, wherein the poly(meth)acrylate polymer chains are poly(glycidylmethacrylate).

12. The adsorption medium as claimed in claim 1, wherein the chromatography matrix is polyethylene terephthalate (PET) or polybutylene terephthalate (PBT) fibers, the polymeric spacer elements are poly(allylamine), poly(meth)acrylate polymer chains are poly(glycidylmethacrylate), and the chromatographically active centers are anionic groups.

13. The adsorption medium as claimed in claim 1, wherein the chromatography matrix is nylon membrane, the polymeric spacer elements are poly(allylamine), the poly(meth)acrylate polymer chains are poly(glycidylmethacrylate), and the chromatographically active centers are anionic groups.

14. The adsorption medium as claimed in claim 1, wherein the chromatography matrix is PET fibers, the polymeric spacer elements are polyvinyl alcohol, the poly(meth)acrylate polymer chains are poly(glycidylmethacrylate), and the chromatographically active centers are anionic groups.

15. The adsorption medium as claimed in claim 1, wherein the anionic groups are sulfonic acid groups.

16. A method for producing an adsorption medium, comprising the steps:

(a) providing a chromatography matrix having a surface, the chromatography matrix selected from the group consisting of natural or synthetic fibers, polymer membranes, nonwovens and wovens;
(b) immobilizing polymeric spacer elements directly chemically or physically on the surface of the chromatography matrix, the polymeric spacer elements having a molecular weight per polymeric spacer element ranging from 5000 to 2,000,000 g/mol, wherein the polymeric spacer elements are selected from the group consisting of polyamines and polyvinyl alcohols; and
(c) immobilizing poly(meth)acrylate polymer chains containing chromatographically active centers chemically on the polymeric spacer elements to produce the adsorption medium, wherein the chromatographically active centers are selected from the group consisting of anionic and cationic groups.

17. The method for producing an adsorption medium as claimed in claim 16, wherein step (c) comprises the steps:

(c1) immobilizing a polymerization initiator on the polymeric spacer elements;
(c2) carrying out a spacer element-initiated polymerization of a monomer to form immobilized poly(meth)acrylate polymer chains on the polymeric spacer elements; and
(c3) optionally modifying the immobilized poly(meth)acrylate polymer chains to form chromatographically active centers on the poly(meth)acrylate polymer chains.

18. The method for producing an adsorption medium as claimed in claim 17, wherein the spacer element-initiated polymerization step (c2) is carried out by means of an atom transfer radical polymerization (ATRP).

19. The method for producing an adsorption medium as claimed in claim 17, wherein use is made in step (c2) of a polymerization solution comprising a portion of not more than 3 mol % of bifunctional monomers, based on the total amount of monomers in the solution.

20. A method of purifying biomolecules using an adsorption medium comprising the steps of:

providing an adsorption medium including a chromatography matrix having a surface, the chromatography matrix selected from the group consisting of natural or synthetic fibers, polymer membranes, nonwovens and wovens; polymeric spacer elements directly chemically or physically bound to the chromatography matrix, the polymeric spacer elements having a molecular weight per polymeric spacer element ranging from 5000 to 2,000,000 g/mol and wherein the polymeric spacer elements are selected from the group consisting of polyamines and polyvinyl alcohols; and poly(meth)acrylate polymer chains containing chromatographically active centers, wherein the chromatographically active centers are selected from the group consisting of anionic and cationic groups and wherein the poly(meth)acrylate polymer chains are chemically bound to the polymeric spacer elements; and
passing a solution containing the biomolecules across the adsorption medium to obtain purified biomolecules.

21. The method as claimed in claim 20, wherein the biomolecules are proteins, peptides, amino acids, nucleic acids, viruses, virus-like particles and/or endotoxins.

* * * * *